United States Patent
Morman et al.

[11] Patent Number: 5,883,028
[45] Date of Patent: Mar. 16, 1999

[54] BREATHABLE ELASTIC FILM/NONWOVEN LAMINATE

[75] Inventors: Michael Tod Morman, Alpharetta; Linda Jeanette Morgan, Dunwoody; Bernard Cohen, Berkeley Lake, all of Ga.

[73] Assignee: Kimberly-Clark Worldwide, Inc., Neenah, Wis.

[21] Appl. No.: 867,507

[22] Filed: May 30, 1997

[51] Int. Cl.⁶ .................................................. B32B 27/12
[52] U.S. Cl. ...................... 442/394; 156/229; 428/198; 428/448; 428/910; 442/382; 442/399; 442/400; 442/401
[58] Field of Search .................... 442/394, 399, 442/400, 401, 382; 428/910, 448, 198; 156/229

[56] References Cited

U.S. PATENT DOCUMENTS

| | | |
|---|---|---|
| 3,692,618 | 9/1972 | Dorschner et al. . |
| 3,849,241 | 11/1974 | Butin et al. . |
| 3,870,593 | 3/1975 | Elton et al. . |
| 4,100,324 | 7/1978 | Anderson et al. . |
| 4,340,563 | 7/1982 | Appel et al. . |
| 4,343,848 | 8/1982 | Leonard, Jr. et al. . |
| 4,425,128 | 1/1984 | Motomura . |
| 4,657,802 | 4/1987 | Morman ................................ 428/152 |
| 4,663,220 | 5/1987 | Wisneski et al. . |
| 4,720,415 | 1/1988 | Wielen et al. . |
| 4,741,949 | 5/1988 | Morman et al. . |
| 4,834,738 | 5/1989 | Kielpikowski et al. . |
| 4,842,596 | 6/1989 | Kielpikowski et al. . |
| 4,892,779 | 1/1990 | Leatherman et al. . |
| 4,902,553 | 2/1990 | Hwang et al. . |
| 4,965,122 | 10/1990 | Morman . |
| 4,981,747 | 1/1991 | Morman . |
| 5,026,363 | 6/1991 | Pratt . |
| 5,114,781 | 5/1992 | Morman . |
| 5,116,662 | 5/1992 | Morman . |
| 5,130,342 | 7/1992 | McAllister et al. . |
| 5,226,992 | 7/1993 | Morman . |
| 5,320,891 | 6/1994 | Levy et al. ............................... 428/108 |
| 5,336,545 | 8/1994 | Morman . |
| 5,383,870 | 1/1995 | Takai et al. . |
| 5,393,599 | 2/1995 | Quantrille et al. ...................... 428/284 |
| 5,411,497 | 5/1995 | Tanzer et al. . |
| 5,425,725 | 6/1995 | Tanzer et al. . |
| 5,451,219 | 9/1995 | Suzuki et al. . |
| 5,529,830 | 6/1996 | Dutta et al. . |
| 5,532,350 | 7/1996 | Cottrell et al. . |
| 5,545,371 | 8/1996 | Lu . |
| 5,549,775 | 8/1996 | Odorzynski . |
| 5,558,658 | 9/1996 | Menard et al. . |
| 5,560,974 | 10/1996 | Langley . |
| 5,614,283 | 3/1997 | Potnis et al. . |

FOREIGN PATENT DOCUMENTS

| | | |
|---|---|---|
| 0589222 | 3/1994 | European Pat. Off. . |
| 0674035 | 9/1995 | European Pat. Off. . |
| 8126663 | 5/1996 | Japan . |
| 9618499 | 6/1996 | WIPO . |

*Primary Examiner*—James J. Bell
*Attorney, Agent, or Firm*—Speckman Pauley Petersen & Fejer

[57] ABSTRACT

A breathable elastic laminate is formed by bonding a film including an elastic water vapor-soluble polymer to a neckable nonwoven web such that when the film is relaxed, the web is in a necked state. The breathable laminate is stretchable in a direction parallel to the narrowing or necking of the web. The laminate possesses excellent water vapor permeability but acts as a barrier to the passage of odor-causing chemicals including ammonia.

45 Claims, 6 Drawing Sheets

BREATHABLE ELASTIC FILM/NONWOVEN LAMINATE

FIELD OF THE INVENTION

This invention is directed to a breathable elastic laminate of a film and a nonwoven web. The laminate is particularly useful as an outer cover for disposable diapers and other personal care disposable products. The laminate is also useful for breathable surgical gowns, and other breathable applications.

BACKGROUND OF THE INVENTION

Various types of vapor permeable, liquid impermeable polymeric films are known in the art. One method of making a polymeric film vapor permeable, involves mixing a matrix polymer with a substantial quantity (e.g., 10–70% by weight) of an organic or inorganic particulate filler such as, for example, calcium carbonate, and extruding a film from the blend. The matrix polymer may include a polyolefin, such as polyethylene or polypropylene, or various olefin copolymers. The film may be a monolayer film, a multilayer film which contains the filled layer as a primary layer along with thin breathable skin layers, or a multilayer film having more than one filled layer. Then, the film is heated and stretched, causing voids to form in the film.

Breathable films are employed as backsheets, or as a backsheet component laminated to a nonwoven web and/or other layers, in many of today's personal care absorbent articles, diapers being one example. Filled, stretched polyolefin films provide good water vapor transmission, making the diapers more comfortable to the wearer. As a result, the relative humidity and temperature within the diaper or other product can be reduced by using breathable films and laminates.

One drawback of the voided filled polyolefin films and laminates is that they transmit ammonia and other odor-causing vapors as well as water vapor. Ammonia is the primary odor-causing ingredient in urine, for instance. Also, the voided polyolefin films and laminates are generally not elastic to any significant extent. Also, any particle agglomerates in the film before stretching can cause large pores which will leak. Fluids which wet such films (alcohols, water with surfactants, etc.) will pass through the holes. Bacteria and viruses can pass through the holes as well. Also, the voids generated during stretching weaken the film.

SUMMARY OF THE INVENTION

The present invention is directed to a breathable elastic film and laminate useful as an outer cover for diapers and other personal care products, and surgical gowns, which have high permeability to water vapor and low permeability to ammonia and some other odor-causing molecules. The film is formed from an elastic polymeric material that water molecules can dissolve into. Instead of relying on molecular diffusion of water vapor through voids or pores in the film, the films and laminates of the invention rely on solubility of water molecules in the solid polymer film, diffusion of water molecules through the solid polymer film, and evaporation of the water passing through the film into the surrounding air. Molecules of water vapor are absorbed into the film from one surface, pass through the film in an absorbed state, and are released from the other surface.

The elastic films do not absorb ammonia to any appreciable extent, and are not microporous or voided. Therefore, ammonia is not transmitted through the films to any significant extent, and ammonia odors are contained.

The film can be formed from any suitable film-forming elastic polymer that exhibits an ability to absorb and diffuse water vapor. Suitable polymers include without limitation vulcanized silicone rubber, other silicone polymers, polyurethanes, polyether esters, and polyether amides.

The laminate of the invention includes at least one breathable elastic film layer and a stretchable nonwoven web such as a necked nonwoven web. The nonwoven web is preferably a spunbonded web, or a laminate which includes a spunbonded web. The film and nonwoven web are bonded together, either thermally, ultrasonically, or with an adhesive, when the web is in an elongated "necked in" condition. Bonding of the unstretched elastic film to the necked in nonwoven web provides a breathable laminate which is stretchable in a direction parallel to the direction of narrowing or necking of the web before lamination, and which partly or filly recovers when the stretching force is removed.

With the foregoing in mind, it is a feature and advantage of the invention to provide a breathable laminate having improved elastic properties.

It is also a feature and advantage of the invention to provide a breathable laminate that is resistant to ammonia odor penetration.

It is also a feature and advantage of the invention to provide an improved breathable laminate useful in a wide variety of diaper outercovers, other personal care products, surgical gowns, and other breathable applications.

The foregoing and other features and advantages of the invention will become further apparent from the following detailed description of the presently preferred embodiments, read in conjunction with the examples and drawings.

DEFINITIONS

The term "elastic" is used herein to mean any material which, upon application of a biasing force, is stretchable, that is, elongatable, to a stretched, biased length which is at least about 160 percent of its relaxed unbiased length, and which, will recover at least 55 percent of its elongation upon release of the stretching, elongating force. A hypothetical example would be a one (1) inch sample of a material which is elongatable to at least 1.60 inches and which, upon being elongated to 1.60 inches and released, will recover to a length of not more than 1.27 inches. Many elastic materials may be stretched by much more than 60 percent of their relaxed length, for example, 100 percent or more, and many of these will recover to substantially their original relaxed length, for example, to within 105 percent of their original relaxed length, upon release of the stretching force.

As used herein, the term "breathable" refers to a film or laminate having a moisture vapor transmission rate (MVTR) of at least about 300 grams/$m^2$-24 hours, measured using ASTM E96-80, upright cup method, with minor variations as described in the Test Procedure below.

As used herein, the term "nonelastic" refers to any material which does not fall within the definition of "elastic," above.

As used herein, the term "recover" refers to a contraction of a stretched material upon termination of a biasing force following stretching of the material by application of the biasing force. For example, if a material having a relaxed, unbiased length of one (1) inch is elongated 50 percent by stretching to a length of one and one half (1.5) inches, the material would be elongated 50 percent (0.5 inch) and would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its one-half (0.5) inch elongation. Recovery may be expressed as [(maximum stretch length—final sample length)/(maximum stretch length—initial sample length)]×100.

As used herein, the term "nonwoven web" means a web that has a structure of individual fibers or threads which are interlaid, but not in an identifiable, repeating manner. Nonwoven webs have been, in the past, formed by a variety of processes such as, for example, melt-blowing processes, spunbonding processes and bonded carded web processes.

As used herein, the term "microfibers" means small diameter fibers having an average diameter not greater than about 100 microns, for example, having a diameter of from about 0.5 microns to about 50 microns, more particularly, microfibers may have an average diameter of from about 4 microns to about 40 microns.

As used herein, the term "meltblown fibers" means fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, the disclosure of which is hereby incorporated by reference.

As used herein, the term "spunbonded fibers" refers to small diameter fibers which are formed by extruding a molten thermoplastic material as filaments from a plurality of fine, usually circular, capillaries of a spinnerette with the diameter of the extruded filaments then being rapidly reduced as by, for example, eductive drawing or other well-known spunbonding mechanisms. The production of spunbonded nonwoven webs is illustrated in patents such as, for example, in U.S. Pat. No. 4,340,563 to Appel et al., and U.S. Pat. No. 3,692,618 to Dorschner et al. The disclosures of both these patents are hereby incorporated by reference.

As used herein, the term "interfiber bonding" means bonding produced by entanglement between individual fibers to form a coherent web structure without the use of thermal bonding. This fiber entangling is inherent in the meltblown processes but may be generated or increased by processes such as, for example, hydraulic entangling or needle punching. Alternatively and/or additionally, a bonding agent can be utilized to increase the desired bonding and to maintain structural coherency of a fibrous web. For example, powdered bonding agents and chemical solvent bonding may be used.

As used herein, the term "sheet" means a layer which may either be a film or a nonwoven web.

As used herein, the term "necked material" refers to any material which has been narrowed in at least one dimension by application of a tensioning force in another direction.

As used herein, the term "neckable material" means any material which can be necked.

As used herein, the term "percent neckdown" refers to the ratio determined by measuring the difference between the un-necked dimension and the necked dimension of the neckable material and then dividing that difference by the un-necked dimension of the neckable material.

As used herein, the term "composite elastic necked-bonded material" refers to a material having an elastic sheet joined to a necked material at least at two places. The elastic sheet may be joined to the necked material at intermittent points or may be completely bonded thereto. The joining is accomplished while the elastic sheet and the necked material are in juxtaposed configuration. The composite elastic necked-bonded material is elastic in a direction generally parallel to the direction of neckdown of the necked material. A composite elastic necked-bonded material may include more than two layers. For example, the elastic sheet may have necked material joined to both of its sides so that a three-layer composite elastic necked-bonded material is formed having a structure of necked material/elastic sheet/necked material, both necked materials being elongated in the same direction. Additional elastic sheets and/or necked material layers may be added. Yet other combinations of elastic sheets and necked materials may be used.

As used herein, the term "palindromic laminate" means a multilayer laminate, for example, a composite elastic necked-bonded material which is substantially symmetrical. Exemplary palindromic laminates would have layer configurations of A/B/A, A/B/B/A, A/A/B/A/A, etc. Exemplary non-palindromic laminates would have layer configurations of A/B/C, A/B/C/A, A/C/B/D, etc.

As used herein, the term "polymer" generally includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, the term "water vapor permeable elastic polymer" refers to an elastic polymer whose films have a water permeability of at least about 150 kg-cm/$(km)^2$-day at 38° C. and 100% relative humidity, measured according to ASTM E96-80, inverted cup method. Further discussion of permeability is provided in the Kirk-Othmer *Encyclopedia Of Chemical Technology*, Third Edition, Volume 3, John Wiley & Sons, pp. 486–496, the disclosure of which is incorporated by reference.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, solvents, particulates and materials added to enhance processability of the composition.

TEST PROCEDURE FOR MEASURING MOISTURE VAPOR TRANSMISSION RATE (MVTR)

A measure of the breathability of a fabric is the moisture vapor transmission rate (MVTR), which for the sample materials is calculated essentially in accordance with ASTM Standard E96-80 with minor variations in test procedure as set forth below. Circular samples measuring three inches in diameter are cut from each of the test materials, and tested along with a control which is a piece of CELGARD® 2500 sheet from Celanese Separation Products of Charlotte, N.C. CELGARD® 2500 sheet is a microporous polypropylene sheet. Three samples are prepared for each material. The test dish is a number 60-1 Vapometer pan distributed by Thwing-Albert Instrument Company of Philadelphia, Pa. One hundred milliliters of water is poured into each Vapometer pan and individual samples of the test materials and control material are placed across the open tops of the individuals pans. Screw-on flanges are tightened to form a seal along the edges of the pan, leaving the associated test material or control material exposed to the ambient atmosphere over a 6.5 centimeter diameter circle having an exposed area of approximately 33.17 square centimeters. The pans are placed in a forced air oven at 100° F. (32° C.) for 1 hour to equilibrate. The oven is a constant temperature oven with external air circulating through it to prevent water vapor accumulation inside. A suitable forced air oven is, for example, a Blue M Power-O-Matic 60 oven distributed by Blue M Electric Company of Blue Island, Ill. Upon completion of the equilibration, the pans are removed from the oven, weighed and immediately returned to the oven. After 24 hours, the pans are removed from the oven and weighed again. The preliminary test water vapor transmission rate values are calculated as follows:

Test MVTR=(grams weight loss over 24 hours)×315.5 g/m$^2$-24 hours

The relative humidity within the oven is not specifically controlled.

Under predetermined set conditions of 100° F. (32° C.) and ambient relative humidity, the MVTR for the CELGARD® 2500 control has been defined to be 5000 grams per square meter for 24 hours. Accordingly, the control sample was run with each test and the preliminary test values were corrected to set conditions using the following equation:

MVTR=(Test MVTR/control MVTR)×(5000 g/m$^2$-24 hours)

DETAILED DESCRIPTION OF THE PRESENTLY PREFERRED EMBODIMENTS

Figure 1:
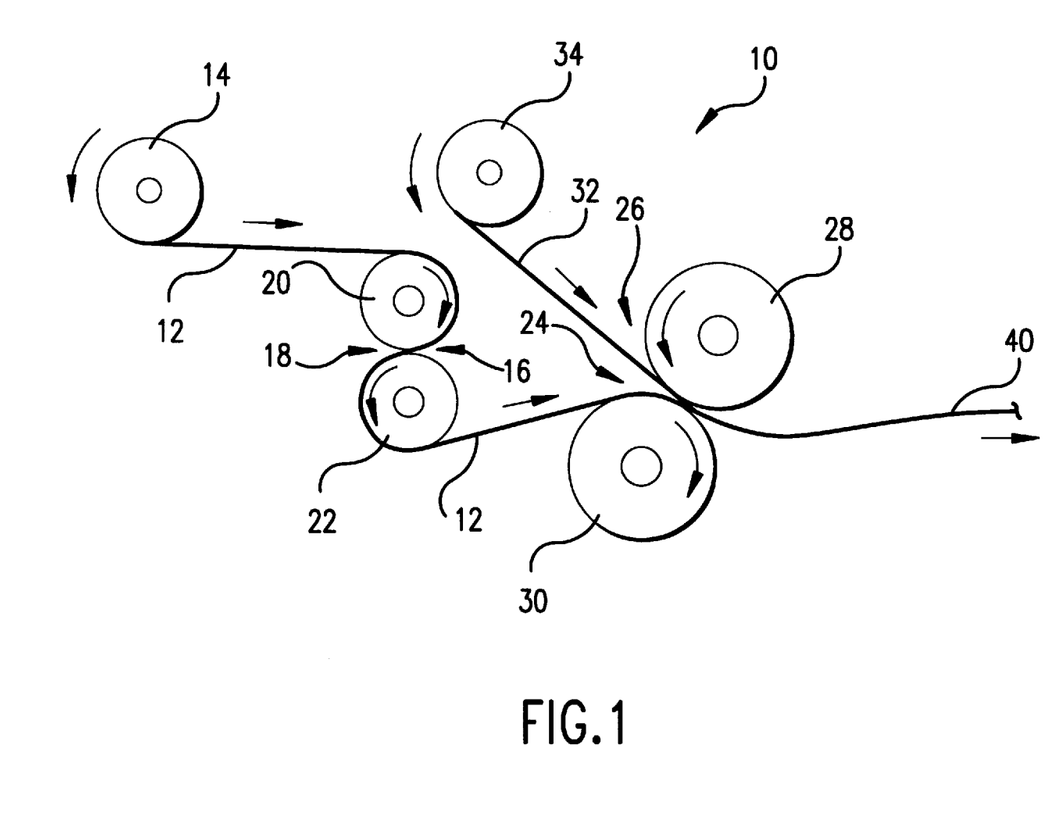
FIG. 1 is a schematic representation of an exemplary process for forming a composite elastic neck-bonded material.

Referring to FIG. 1 of the drawings there is schematically illustrated at 10 a process for forming a composite elastic necked-bonded breathable laminate material. A neckable material 12 is unwound from a supply roll 14 and travels in the direction indicated by the arrow associated therewith as the supply roll 14 rotates in the direction of the arrows associated therewith. The neckable material 12 passes through a nip 16 of the drive roller arrangement 18 formed by the drive rollers 20 and 22.

The neckable material 12 may be formed by known spunbonding processes, and passed directly through the nip 16 without first being stored on a supply roll.

A breathable elastic sheet 32 including a water vapor-soluble polymer is unwound from a supply roll 34 and travels in the direction indicated by the arrow associated therewith as the supply roll 34 rotates in the direction of the arrows associated therewith. The elastic sheet passes through the nip 24 of the bonder roller arrangement 26 formed by the bonder rollers 28 and 30. The elastic sheet 32 may be formed by extrusion processes such as, for example, film extrusion processes and passed directly through the nip 24 without first being stored on a supply roll.

The breathable elastic sheet made from the water vapor-permeable polymer should have a moisture vapor transmission rate (MVTR) of at least about 300 grams/m$^2$-24 hours, preferably at least about 1200 grams/m$^2$-24 hours, most preferably at least about 2000 grams/m$^2$-24 hours. The MVTR is a function of both film thickness and polymer type. Preferred elastic polymers which exhibit the required MVTR over a range of useful film thicknesses include without limitation vulcanized silicone rubber, some other silicone polymers, polyurethanes, polyether esters and polyether amides. The following Table 1 gives representative water vapor permeabilities of exemplary elastic polymers.

TABLE 1

| Polymer Type | Water Vapor Permeability, kg-cm/(km)$^2$-day |
|---|---|
| Vulcanized silicone rubber | 11,900 |
| Polyurethane-Estane ® 58237 | 760 |
| Polyurethane-Estane ® 58245 | 1,270 |
| Polyether amide-PEBAX ® | 830 |
| Polyether ester-Hytrel ® or Arnitel ® | 930 |
| Polyester-polyurethane copolymer | 160 |
| Polyether-polyurethane copolymer | 310 |

If the elastic polymer has low water vapor permeability, the film may have to be extremely thin in order to achieve the desired minimum level of MVTR. The production and use of very thin films may be impractical due to low film strength and processing difficulties. The elastic polymer itself should therefore have sufficient water vapor permeability to allow the use of films having practical thicknesses. Preferably, the elastic polymer will have a water vapor permeability of at least about 150 kg-cm/(km)$^2$-day, more preferably at least about 500 kg-cm/(km)$^2$-day, most preferably at least about 1000 kg-cm/(km)$^2$-day.

Figure 5:
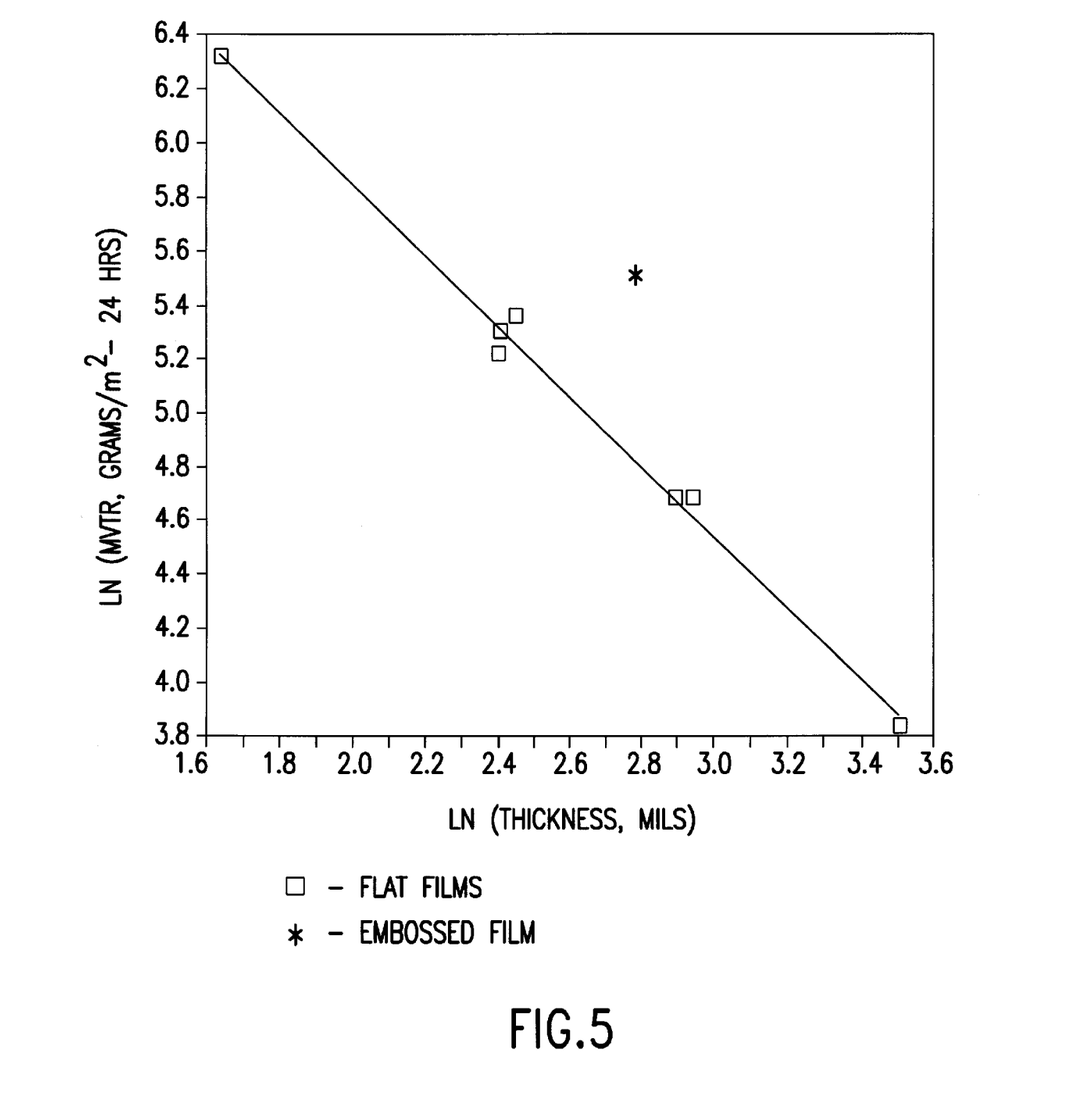
FIG. 5 shows the relationship between vapor permeability and thickness for films made of vulcanized silicone rubber.

In addition to being water vapor-permeable, the breathable elastic film should not be so thick as to substantially impair its water vapor transmission. The MVTR of a particular composition of film is roughly inversely related to its thickness if there are no molecular interactions between the film and the vapor. For water vapor permeable films, this relationship may vary due to the affinity of the water with the films. FIG. 5 shows the relationship between the logarithm of film thickness (mils) and the logarithm of moisture vapor transmission rate, MVTR (grams/m$^2$-24 hrs), for films made from vulcanized silicone rubber. The MVTR was tested using ASTM E96-80, upright cup method, with minor variations as described in the Test Procedure above. Using linear regression techniques on the six data points shown, the MVTR was found to be related to film thickness as follows:

MVTR(g/m$^2$-24 hrs)=4700×(thickness, mils)$^{-1.3}$

Thus, a two-mil thick film of vulcanized silicone rubber should have an MVTR of about 2000 grams/m$^2$-24 hrs.

Generally, the film thickness for any elastic water vapor-permeable polymer should be selected to give an MVTR of at least about 300 grams/m$^2$-24 hrs, preferably at least about 1200 grams/m$^2$-24 hrs, most preferably at least about 2000 grams/m$^2$-24 hrs when the film is in the unstretched state. Elastic polymers having somewhat less water vapor permeability than vulcanized silicone rubber should therefore be made into thinner films in order to achieve comparable vapor transmission. For instance, the unstretched elastic vapor permeable film may be less than about 1 mil thick, or less than about 0.5 mil thick, or less than about 0.3 mil thick depending on the strength of the film and the water vapor permeability of the polymer.

The elastic water vapor-permeable polymer films may be crosslinked or thermoplastic, depending on the polymer. Vulcanized silicone rubber is preferably crosslinked to provide sufficient film strength. The crosslinking can be accomplished by applying heat treatment such as by placing films in an oven. Polyurethanes may be thermoplastic or crosslinked. Polyether esters, and polyether amides, are generally thermoplastic.

Figure 6:
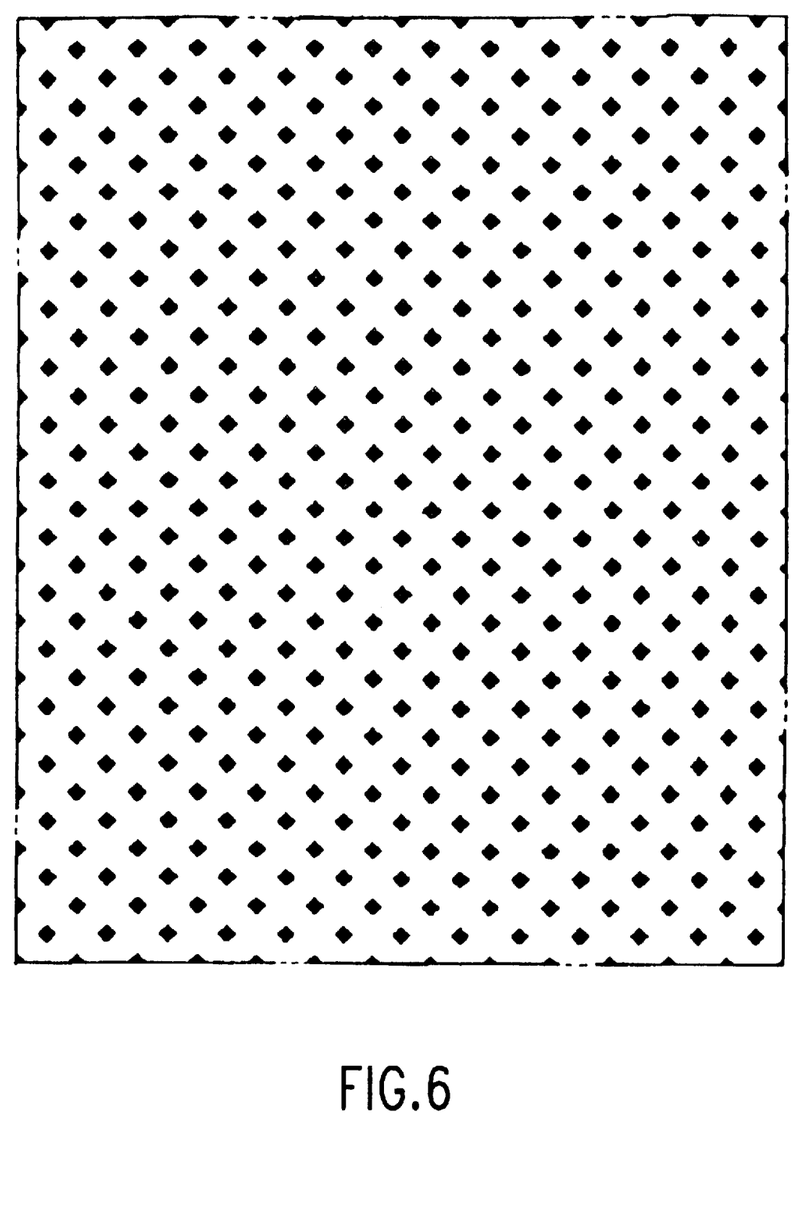
FIG. 6 shows a delta dot embossing/bonding pattern.

In a preferred embodiment, the elastic film may be embossed to further increase its MVTR. Any polymer that can be made into an elastic film, embossed, and which retains at least some of the embossed pattern will exhibit this improvement. Some polymers, such as silicone rubber, can be crosslinked to lock in the embossed pattern. One suitable embossing pattern is a "delta dot" pattern shown in FIG. 6, which is a pattern of solid diamonds or squares imprinted into a film using a conventional embossing technique. A film embossed with a delta dot pattern is thinner in the "windows" defined by the imprinted squares, than in the "frames" or nonembossed regions surrounding the windows. If the MVTR is inversely related to thickness, or related according to the equation given above, then the embossing serves to increase the MVTR in the imprinted "window" regions versus the nonembossed regions, and effectively increases the overall MVTR for the film.

FIG. 5 shows the MVTR for an embossed film sample of vulcanized silicone rubber having a thickness of 19 mils in the frame regions, a thickness of only 3.2 mils in the window regions caused by the embossed delta dot pattern, and an overall (average) thickness of about 16 mils. This film sample is designated with an asterisk (*) in FIG. 5. The MVTR for the embossed film sample is substantially higher than for a flat vulcanized silicone rubber film having the same overall thickness, as indicated by the position of the asterisk substantially above the line.

The spunbond web component of the laminate is typically open and porous, and does not significantly affect the breathability of the laminate. In other words, the moisture breathability of the film should determine the breathability of the laminate. However, care should be taken to bond the film and web together using techniques that do not significantly disrupt the breathability of the laminate. If an adhesive is used, the adhesive should cover only a portion of the total film area, and should be applied as thinly as possible. The preferred adhesive for attaching polyether ester or polyurethane films to a spunbonded web is a reactive polyurethane-based adhesive available from Shawmut Mills in Bridgewater, Mass. When used, an adhesive should be applied at a basis weight less than about 5.0 grams per square meter (gsm), preferably less than about 1.0 gsm, most preferably less than about 0.5 gsm. The adhesive should preferably cover not more than about 75% of the film surface unless the adhesive itself is very water permeable.

When thermal bonding is employed, the bonding conditions should be such that the spunbond web is not unnecessarily compressed or fused together, and the film is not damaged or distorted in a way that significantly impairs moisture breathability. Thermal calender bonding is a preferred technique, using a spaced apart bond pattern that attaches the web and film together at less than about 25% of the total interfacial area, preferably less than about 20% of the total interfacial area, most preferably less than about 15% of the total interfacial area.

In the process shown in FIG. 1, the neckable spunbond web 12 passes through the nip 16 of the S-roll arrangement 18 in a reverse S-path as indicated by the rotation direction arrows associated with the stack rollers 20 and 22. From the S-roll arrangement 18, the neckable web 12 passes through the pressure nip 24 formed by a bonder roller arrangement 26. Because the peripheral linear speed of the rollers of the S-roll arrangement 18 is controlled to be less than the peripheral linear speed of the rollers of the bonder roller arrangement 26, the neckable web 12 is tensioned between the S-roll arrangement 18 and the pressure nip of the bonder roll arrangement 26. By adjusting the difference in the speeds of the rollers, the neckable web 12 is tensioned so that it necks a desired amount and is maintained in such tensioned, necked condition while the breathable elastic sheet 32 is joined to the necked web 12 during their passage through the bonder roller arrangement 26 to form a composite elastic necked-bonded laminate 40.

Other methods of tensioning the neckable web 12 may be used such as, for example, tenter frames or other cross-machine direction stretcher arrangements that expand the neckable web 12 in other directions such as, for example, the cross-machine direction so that, after bonding to the breathable elastic sheet 32, the resulting composite elastic necked-bonded material 40 will be elastic in a direction generally parallel to the direction of necking, i.e., in the machine direction.

The neckable web 12 may be a porous nonwoven material such as, for example, spunbonded web, meltblown web or bonded carded web. If the neckable material is a web of meltblown fibers, it may include meltblown microfibers. The neckable material 12 may be made of fiber forming polymers such as, for example, polyolefins. Exemplary polyolefins include one or more of polypropylene, polyethylene, ethylene copolymers, propylene copolymers, and butene copolymers. Useful polypropylenes include, for example, polypropylene available from the Exxon Chemical Company under the trade designation Exxon 3445, and polypropylene available from the Shell Chemical Company under the trade designation DX 5A09.

In one embodiment of the present invention, the neckable web 12 is a multilayer material having, for example, at least one layer of spunbonded web joined to at least one layer of meltblown web, bonded carded web or other suitable material. For example, neckable material 12 may be a multilayer material having a first layer of spunbonded polypropylene having a basis weight from about 0.2 to about 8 ounces per square yare (osy), a layer of meltblown polypropylene having a basis weight from about 0.2 to about 4 osy, and a second layer of spunbonded polypropylene having a basis weight of about 0.2 to about 8 osy. Alternatively, the neckable web 12 may be single layer of material such as, for example, a spunbonded web having a basis weight of from about 0.2 to about 10 osy or a meltblown web having a basis weight of from about 0.2 to about 8 osy.

The neckable material 12 may also be a composite material made of a mixture of two or more different fibers or a mixture of fibers and particulates. Such mixtures may be formed by adding fibers and/or particulates to the gas stream in which meltblown fibers are carried so that an intimate entangled commingling of meltblown fibers and other materials, e.g., wood pulp, staple fibers and particulates such as, for example, hydrocolloid (hydrogel) particulates commonly referred to as superabsorbent materials, occurs prior to collection of the meltblown fibers upon a collecting device to form a coherent web of randomly dispersed meltblown fibers and other materials such as disclosed in U.S. Pat. No. 4,100,324, the disclosure of which is hereby incorporated by reference.

If the neckable web 12 is a nonwoven web of fibers, the fibers should be joined by interfiber bonding to form a coherent web structure which is able to withstand necking. Interfiber bonding may be produced by entanglement between individual meltblown fibers. The fiber entangling is inherent in the meltblown process but may be generated or increased by processes such as, for example, hydraulic entangling or needlepunching. Alternatively and/or additionally a bonding agent may be used to increase the desired bonding.

The elastic sheet 32 may also be a multilayer material in that it may include two or more individual coherent webs or films. Additionally, the elastic sheet 12 may be a multilayer material in which one or more of the layers contain a mixture of elastic and nonelastic fibers or particulates.

The bonder roller arrangement 26 may include a patterned calender roller, such as, for example, a pin embossing roller arranged with a smooth anvil roller. One or both of the calender roller and the smooth anvil roller may be heated and the pressure between these two rollers may be adjusted by well-known means to provide the desired temperature, if any, and bonding pressure to join the necked material 12 to the elastic sheet 32 forming a composite breathable elastic necked-bonded material 40.

Figure 4:
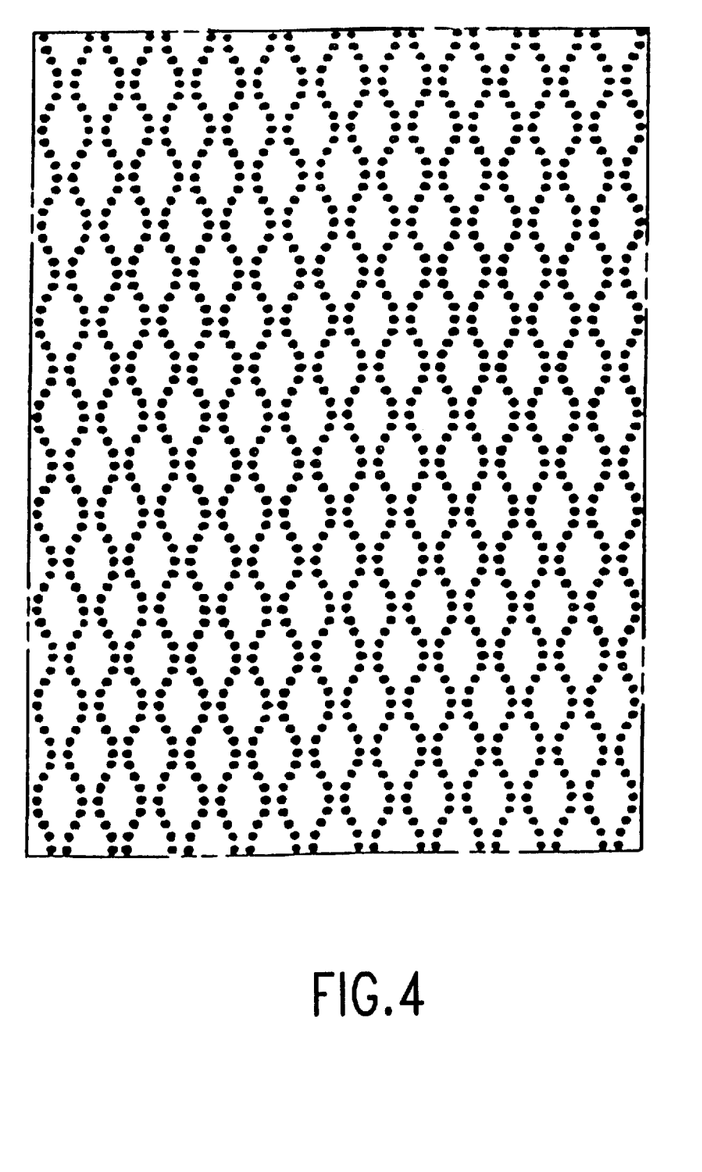
FIG. 4 is a representation of an exemplary bonding pattern used to join layers of a composite elastic neck-bonded material.

The necked material and the elastic sheet may be completely bonded together and still provide a composite elastic necked-bonded material with good stretch properties. That is, a composite elastic material may be formed by joining a necked material to an elastic sheet utilizing bonding surfaces such as, for example, the sinusoidal bonding pattern shown in FIG. 4. That pattern has approximately 75 pins per square inch with each pin about 0.059 inches in diameter, providing a bond surface area of about 20.5 percent.

Necked materials may be joined to the breathable elastic sheet 32 at least at two places by any suitable means such as, for example, thermal or adhesive bonding or ultrasonic welding which softens at least portions of at least one of the materials, usually the elastic sheet because the elastomeric materials used for forming the elastic sheet 32 have a lower softening point that the components of the necked material 12. Joining may be produced by applying heat and/or pressure to the overlaid elastic sheet 32 and the necked material 12 by heating these portions (or the overlaid layer) to at least the softening temperature of the material with the lowest softening temperature to form a reasonably strong and permanent bond between the re-solidified softened portions of the elastic sheet 32 and the necked material 12. Conditions should not be so severe as to perforate the film.

Elastic sheets can be used having basis weights less than 0.5 osy (ounces per square yard), for example, from about 0.25 to about 0.4 osy. Such extremely low basis weight sheets are advantageous because of higher breathability and economic reasons, and are particularly useful in disposable products. Additionally, elastic sheets having higher basis weights such as, for example, from about 0.5 to about 10 osy may also be used.

With regard to thermal bonding, one skilled in the art will appreciate that the temperature to which the materials, or at least the bond sites thereof, are heated for heat-bonding will depend not only on the temperature of the heated roll(s) or other heat sources but on the residence time of the materials on the heated surfaces, the basis weights of the materials and their specific heats and thermal conductivities. However, for a given combination of materials, and in view of the herein contained disclosure the processing conditions necessary to achieve satisfactory bonding can be readily determined by one of skill in the art.

Conventional drive means and other conventional devices which may be utilized in conjunction with the apparatus of FIG. 1 are well known and, for purposes of clarity, have not been illustrated in the schematic view of FIG. 1.

The relation between the original dimensions of the neckable material 12 to its dimensions after tensioning determines the approximate limits of stretch of composite elastic necked-bonded material. Because the neckable material 12 is able to stretch and return to its necked dimensions in directions such as, for example the machine direction or the cross-machine direction, the composite elastic necked-bonded material will be stretchable in generally the same direction as the neckable material 12.

Figure 2:
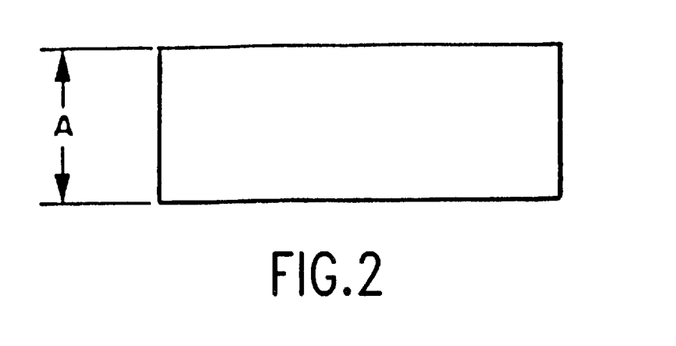
FIG. 2 is a plan view of an exemplary neckable material before tensioning and necking.
Figure 2A:
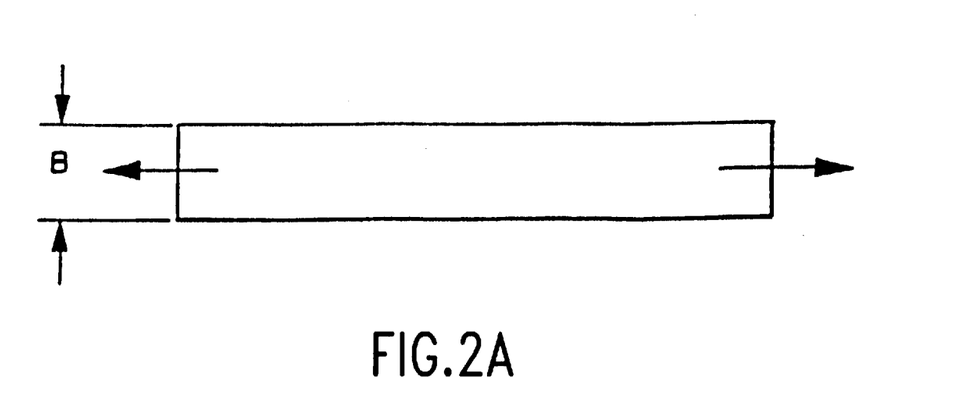
FIG. 2A is a plan view of an exemplary necked material.
Figure 2B:
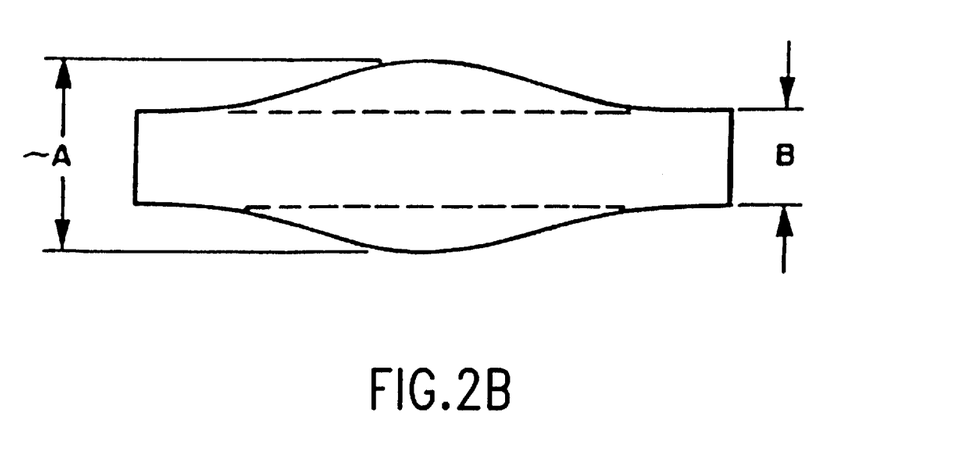
FIG. 2B is a plan view of an exemplary composite elastic neck-bonded material while partially stretched in the cross-machine direction.

For example, with reference to FIGS. 2, 2A, and 2B, if it is desired to prepare a composite elastic necked-bonded material stretchable to a 150% elongation, a width of neckable material shown schematically and not necessarily to scale in FIG. 2 having a width "A" such as, for example, 250 cm, is tensioned so that it necks down to a width "B" of about 100 cm. The necked material shown in FIG. 2A is then joined to an elastic sheet (not shown) having a width of approximately 100 cm and which is at least stretchable to a width of 250 cm. The resulting composite elastic necked-bonded material shown schematically and not necessarily to scale in FIG. 2B has a width "B" of about 100 cm and is stretchable to at least the original 250 cm width "A" of the neckable material for an elongation of about 150%. As can be seen from the example, the elastic limit of the elastic sheet needs only to be as great as the minimum desired elastic limit of the composite elastic necked-bonded material.

Figure 3:
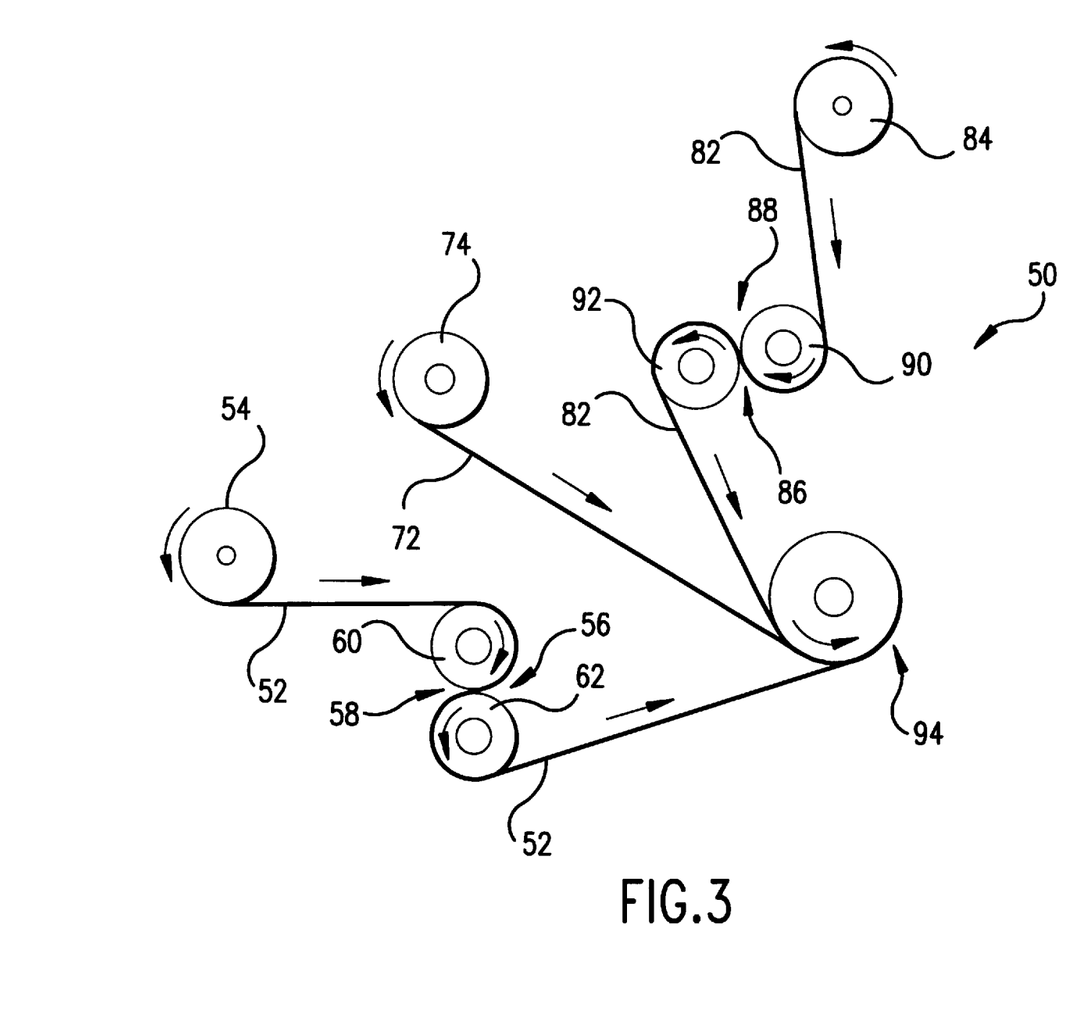
FIG. 3 is a schematic representation of an exemplary process for forming a composite elastic neck-bonded material using a tensioned wind-up method.

Referring now to FIG. 3 of the drawings, there is schematically illustrated at 50 an exemplary process for forming a composite elastic necked-bonded material by a tensioned wind-up method. A first neckable material 52 is unwound from a supply roll 54 and a second neckable material 82 is unwound from a supply roll 84. The neckable materials 52 and 82 then travel in the direction indicated by the arrows associated therewith as the supply rolls 54 and 84 rotate in the direction of the arrows associated therewith. The neckable material 52 then passes through the nip 56 of an S-roll arrangement 58 formed by the stack rollers 60 and 62. Likewise, the neckable material 82 passes through the nip 86 of an S-roll arrangement 88 formed by the stack rollers 90 and 92. The neckable materials 52 and 82 may be formed by known nonwoven extrusion processes such as, for example, known spunbonding and/or known meltblowing processes and passed through the nips 56 and 86 without first being stored on supply rolls.

An elastic sheet 72 is unwound from a supply roll 74 and travels in the direction indicated by the arrow associated therewith as supply roll 74 rotates in the direction of the arrows associated therewith. The elastic sheet 72 may be formed by known extrusion processes such as, for example, cast film or blown film extrusion processes without first being stored on a supply roll.

The neckable material 52 then passes through a nip 56 of an S-roll arrangement 58 in a reverse-S wrap path as indicated by the rotation direction of the arrows associated with the stack rollers 60 and 62. Likewise, the neckable material 82 passes through a nip 86 of an S-roll arrangement 88 in a reverse-S wrap path as indicated by the rotation direction arrows associated with the stack rollers 90 and 92. Because the peripheral linear speeds of the rollers of the S-roll arrangements 58 and 88 are controlled to be lower than the peripheral linear speed of the rollers of the wind-up roll 94, the neckable materials 52 and 82 are necked and tensioned so that they sandwich the elastic sheet 72 as they are wound up on the wind-up roll 94.

The above-described tensioned wind-up bonding methods are suited for low basis weight elastomeric sheets. For example, elastic sheets may be used having basis weights less than 0.5 osy (ounces per square yard), for example, from about 0.25 to about 0.4 osy. Such extremely low basis weight sheets are useful for economic reasons, particularly in disposable products. Additionally, elastic sheets having higher basis weights such as, for example, from about 0.5 to about 10 osy may also be used. The elastic sheet can also be extruded right onto the necked nonwoven web.

With regard to the bonding pressure utilized when bonding is effected by the above-described tensioned wind-up method, specification of a bonding pressure does not, in itself, take into account complicating factors such as, for example, the bonding compatibility of elastic sheet and the necked materials and/or the basis weight weights of the materials. Nonetheless, one skilled in the art, taking into account such factors will readily be able to appropriately select and vary an effective bonding pressure.

Conventional drive means and other conventional devices which may be utilized in conjunction with the apparatus of FIG. 3. are well known and, for purposes of clarity, have not been illustrated in the schematic view of FIG. 3.

In one embodiment, the breathable elastic film 32 may be prebonded to another breathable elastic layer before being laminated to the neckable web 12. For instance, the breathable film 12 may be a thin layer of polyether ester sold under the trade name Hytrel, by the DuPont Company, located in Wilmington, Del. The film 12 may be combined with a meltblown layer made by Kimberly-Clark Corporation of another polyether ester sold under the trade name Arnitel, by the DSM Company of Evansville, Ind. This combination gives excellent water vapor permeability. The meltblown web should have a basis weight of about 10–75 gsm, preferably about 15–50 gsm, most preferably about 20–40 gsm. Preferably, the meltblown filaments are about 10–30 microns in diameter. The combined film and meltblown web may then be laminated to a necked spunbond web to provide a laminate having excellent water vapor permeability and ammonia odor barrier, high hydrohead, one directional elasticity, and a soft feel.

The meltblown web of polyether ester adds considerable strength to the film 12 without impairing its breathability. The film 12 may be bonded to the meltblown web using a conventional bonding technique, for instance, an adhesive print bonding process known to persons skilled in the art. The final laminate may have the configuration elastic meltblown web/elastic film/necked spunbond web or may have the configuration elastic film/elastic meltblown web/necked spunbond web. Also, as long as the meltblown web is porous, it need not include a water vapor soluble polymer, but can be made of any elastic polymer, for example Kraton brand styrene-butudiene rubbers.

In another embodiment of the invention, the breathable elastic film or laminate may be stretched in a direction other than parallel (e.g., perpendicular) to the direction of necking of the nonwoven web, and laminated to the web in a plurality of spaced apart locations while in the stretched condition and while the web is necked. After lamination, the elastic film or laminate is relaxed, causing puckering or gathering of the web between the bonded regions. The resulting composite laminate is stretchable in at least two nonparallel directions. The stretchability of the composite in the directions parallel to the direction of necking is facilitated by the necking of the web. The stretchability of composite in the direction nonparallel (e.g., perpendicular) to the direction of necking is facilitated by the gathering of the web in that direction. Processes for making a multidirectional stretchable laminate from an elastic film and necked nonwoven web are described in U.S. Pat. Nos. 5,116,662 and 5,114,781, both issued to Morman, the disclosures of which are incorporated herein by reference.

Using an unnecked nonwoven web for the above-described process would produce a laminate that stretches only in the direction that the elastic sheet was stretched prior to bonding. Such a process, and a resulting laminate, are described in U.S. Pat. No. 4,720,415, issued to Vander Wielen et al.

Other layer combinations are also possible for the breathable elastic laminate of the invention. Regardless of the configuration and number of layers, the breathable elastic laminate should include at least one breathable elastic film and at least one necked nonwoven (preferably spunbond) layer. Additives such as odor absorbing chemicals (e.g., ammonia absorbing chemicals) may also be included in the laminate. Such additives may be added as particles during formation of the elastic film by cast extrusion, for instance. The additives may be included in an amount up to 80% by weight of the film, preferably about 20–60% by weight of the film. Useful odor absorbing additives include zeolites, other absorbing additives and combinations thereof.

EXAMPLE 1

A piece of unvulcanized Silastic® silicone rubber sheeting from Dow Corning Corp. of Midland, Mich. was embossed with a large delta dot pattern. The delta dots (windows) covered 16% of the total film area, while the unembossed regions (frames) between the dots covered 84% of the total film area. The film was vulcanized in a heated oven to lock in the embossed pattern. The vulcanized film had thicknesses of 19 mils in the frame areas, 3.2 mils in the window areas, and 16.1 mils as a weighted average.

The MVTR of the film was measured using ASTM E96-80 (upright cup method), modified slightly as described above, and was found to be 249 grams/m$^2$-24 hours. A flat film of the same thickness (16.1 mils) would be expected to give an MVTR of only 127 grams/m$^2$-24 hours, calculated from the equation derived from the data in FIG. 5 and set forth below:

$$MVTR = 4700 \times (\text{thickness, mils})^{-1.3}$$

From the same equation, it can be expected that a completely flat film would have to have a thickness of only 9.6 mils in order to have an MVTR of 249 grams/m$^2$-24 hours. Thus, by embossing the film, substantially higher MVTR's typical of much thinner films can be achieved.

Notably, the MVTR of the embossed film can be predicted from the same equation, by treating the embossed and nonembossed regions as separate areas in proportion to the total area.

$$\text{Predicted MVTR} = .84(4700)(19)^{-1.3} + .16(4700)(3.2)^{-1.3}$$
$$= .84(102) + .16(1036)$$
$$= 86 + 165 = 251 \text{ grams/m}^2\text{-24 hours}$$

The predicted MVTR of 251 grams/m²-24 hours is essentially the same as the measured MVTR of 249 grams/m²-24 hours. From the equation, it is seen that about two-thirds of the vapor transmission passes through the window regions, even though they constitute only 16% of the total film area.

EXAMPLE 2

A Hytrel® 8171 (polyether ester) film having an unstretched thickness of 1 mil was adhesively laminated to a Arnitel® (polyether ester) nonwoven meltblown web using a reactive polyurethane adhesive. This laminate was then bonded to a reversibly necked spunbonded polypropylene material using a proprietary spray adhesive sold by the 3M Corporation under the trade name Super 77®. Reversibly necked materials are described in U.S. Pat. Nos. 4,981,747 and 4,965,122, both issued to Morman, the disclosures of which are incorporated by reference. The web used had a starting basis weight of 0.8 osy and was necked from a width of 17.75 inches to a width of 8.5 inches, and heat set in the necked condition. The resulting three-layer laminate had a soft outer cover from the necked spunbond layer, good elastic properties from the polyether ester film and meltblown layer, good total film barrier properties (evidenced by a hydrohead exceeding 120 cm, measured using AATCC 127-89) from the polyether ester film, and excellent water vapor transmission (evidenced by an MVTR of 3200 grams/m²-24 hrs) because of the open spunbond and meltblown structures and high moisture permeability of the polyether ester making up the film. The MVTR was measured using ASTM E96-80 (upright cup method), modified slightly as described above.

EXAMPLE 3

This example was performed to test the ammonia odor barrier for a breathable elastic polyurethane film versus a prior art breathable microporous film. Two of the test dishes (cups) typically used to measure MVTR (described in the Test Procedure above) were each partially filled with about 50 cc of a commercial ammonia-based cleaner identified as "Lemon Fresh Parsons Ammonia All Purpose Cleaner." A sample of 1-mil thick Dow Affinity® PL-1845-based microporous polyolefin film was positioned over one cup and sealed. Dow Affinity® PL-1845 is a metallocene-catalyzed linear low density polyethylene (LLDPE). The LLDPE was rendered microporous by combining the resin with more than 50% by weight of a calcium carbonate filler, melt blending the two components, extruding a film from the blend and stretching the extruded film in one direction. A sample of 1-mil thick breathable elastomeric polyurethane blown film was positioned over the other cup and sealed. The microporous LLDPE-based film had an MVTR of about 4000 grams/m²-24 hours. The elastomeric polyurethane had an MVTR of about 1800 grams/m²-24 hours.

Three people were asked to smell each sealed cup. All three people could smell the ammonia very strongly from the cup covered with the LLDPE-based film. All three people could detect only a faint lemon scent from the cup covered with the polyurethane film. This result suggests that the polyurethane allows passage of water vapor and the lemon scent but not the ammonia, and provides an ammonia barrier not existing in the microporous filled LLDPE film.

While the embodiments disclosed herein are presently considered preferred, various modifications and improvements can be made without departing from the spirit and scope of the invention. The scope of the invention is indicated by the appended claims, and all changes that fall within the meaning and range of equivalency are intended to be embraced therein.

We claim:

1. A breathable elastic laminate, comprising
   a breathable elastic film; and
   a neckable nonwoven web bonded to the film while the nonwoven web is necked and the film is in an unstretched state;
   the laminate having an MVTR of at least about 300 grams/m²-24 hrs.
2. The laminate of claim 1, wherein the film comprises a silicone polymer.
3. The laminate of claim 2, wherein the silicone polymer comprises vulcanized silicone rubber.
4. The laminate of claim 1, wherein the film comprises a polyurethane.
5. The laminate of claim 1, wherein the film comprises a polyether ester.
6. The laminate of claim 1, wherein the film comprises a polyether amide.
7. The laminate of claim 1, wherein the film comprises a polymer which has a water vapor permeability of at least about 150 kg-cm/(km)²-day at 38° C. and 100% relative humidity.
8. The laminate of claim 1, wherein the film comprises a polymer which has a water vapor permeability of at least about 500 kg-cm/(km)²-day at 38° C. and 100% relative humidity.
9. The laminate of claim 1, wherein the nonwoven web comprises a spunbond web.
10. The laminate of claim 1, wherein the film comprises a polymer which has a water vapor permeability of at least about 1000 kg-cm/(km)²-day at 38° C. and 100% relative humidity.
11. The laminate of claim 9, wherein the spunbond web comprises polypropylene.
12. The laminate of claim 1, having an MVTR of at least about 1200 g/m²-24 hrs.
13. The laminate of claim 1, having a MVTR of at least about 2000 g/m²-24 hrs.
14. The laminate of claim 1, comprising a second nonwoven web.
15. The laminate of claim 1, wherein the film is embossed.
16. The laminate of claim 1, wherein the film substantially blocks the passage of ammonia odor.
17. A diaper outercover comprising the laminate of claim 1.
18. A surgical gown comprising the laminate of claim 1.
19. A breathable elastic laminate, comprising:
   a water vapor-permeable elastic film comprising a polymer selected from the group consisting of silicone polymers, polyurethanes, polyether esters, polyether amides and combinations thereof; and
   a neckable spunbond web bonded to the film so that the spunbond web is necked when the film is unstretched;
   the laminate having an MVTR of at least about 1200 grams/m²-24 hrs.
20. The laminate of claim 19, wherein the polymer comprises vulcanized silicone rubber.
21. The laminate of claim 19, wherein the film has a thickness not greater than about 1.0 mil, in an unstretched condition.

22. The laminate of claim 19, wherein the film has a thickness not greater than about 0.5 mil, in an unstretched condition.

23. The laminate of claim 19, wherein the film has a thickness not greater than about 0.3 mil, in an unstretched condition.

24. The laminate of claim 19, wherein the film and web are thermally bonded together.

25. The laminate of claim 19, wherein the film and web are adhesively bonded together.

26. The laminate of claim 19, wherein the spunbond web is naked and the film is in an unstretched state when the web and film are bonded together.

27. The laminate of claim 19, wherein the film further comprises one or more odor absorbing chemicals.

28. The laminate of claim 27, wherein the one or more odor absorbing chemicals comprise an ammonia absorbing chemical.

29. The laminate of claim 19, wherein the film is embossed.

30. The laminate of claim 19, comprising an additional nonwoven web.

31. The laminate of claim 19, wherein the film substantially blocks the passage of ammonia odor.

32. A diaper outercover comprising the laminate of claim 19.

33. A surgical gown comprising the laminate of claim 19.

34. A breathable elastic laminate, comprising:
a breathable elastic film having first and second sides;
a meltblown nonwoven layer bonded to the first side of the film; and
a spunbond nonwoven layer bonded to the second side of the film so that the spunbond web is necked when the film is unstretched.

35. The laminate of claim 34, wherein the film comprises a polyether ester.

36. The laminate of claim 34, wherein the meltblown nonwoven layer comprises a polyether ester.

37. The laminate of claim 34, wherein the film and meltblown nonwoven layer each comprise a polyether ester.

38. The laminate of claim 34, wherein the film and meltblown nonwoven layer comprise two different polyether esters.

39. The laminate of claim 34, wherein the film is embossed.

40. A breathable elastic laminate, comprising:
a breathable elastic film; and
a neckable nonwoven laminate bonded to the film so that the nonwoven laminate is necked when the film is unstretched;
the laminate having an MVTR of at least about 300 grams/m$^2$-24 hours.

41. The breathable elastic laminate of claim 40, wherein the neckable nonwoven laminate comprises a film and a meltblown web.

42. The breathable elastic laminate of claim 41, wherein the film comprises polyether ester.

43. The breathable elastic laminate of claim 41, wherein the meltblown web comprises polyether ester.

44. A breathable elastic laminate, comprising:
a breathable elastic film; and
a neckable nonwoven web bonded to the film;
the nonwoven web being necked in a first direction when the film is in an unstretched state;
the film and web being bonded together while the film is stretched in a second direction nonparallel to the first direction.

45. The breathable elastic laminate of claim 44, wherein the second direction is substantially perpendicular to the first direction.

* * * * *